United States Patent [19]

Klausz

[11] Patent Number: 4,530,109
[45] Date of Patent: Jul. 16, 1985

[54] TOMODENSITOMETRY PROCESS AND TOMODENSITOMETER SUITABLE FOR THIS PROCESS

[75] Inventor: Remy Klausz, Paris, France

[73] Assignee: Compagnie Generale de Radiologie, Paris, France

[21] Appl. No.: 437,490

[22] Filed: Oct. 28, 1982

Related U.S. Application Data

[63] Continuation-in-part of Ser. No. 144,905, Apr. 29, 1980, abandoned.

[30] Foreign Application Priority Data

May 2, 1979 [FR] France ............................. 79 11019

[51] Int. Cl.³ ............................................. G03B 41/16
[52] U.S. Cl. ............................................ 378/8; 378/95
[58] Field of Search ....................... 378/8, 16, 95, 114

[56] References Cited

U.S. PATENT DOCUMENTS

| 3,952,201 | 4/1976 | Hounsfield | 378/8 |
| 4,126,785 | 11/1978 | Hounsfield | 378/8 |
| 4,182,311 | 1/1980 | Seppi et al. | 378/8 |
| 4,206,363 | 6/1980 | Hounsfield et al. | 378/8 |

Primary Examiner—Alfred E. Smith
Assistant Examiner—Carolyn E. Fields
Attorney, Agent, or Firm—Oblon, Fisher, Spivak, McClelland & Maier

[57] ABSTRACT

Tomodensitometer, particularly for examining bodies which perform cyclic movements such as the heart and the pericardiac tissues. To eliminate blurring caused by the heart movements the rotation of the radiodensitometric measuring system is synchronized with the movements in such a way that at the time when the periodic movement of the tissue is at its maximum amplitude the projection direction substantially coincides with the direction of the movement and that the start and finish of the measurements coincide respectively with the start and finish of the immobility periods adjacent to the movement period.

7 Claims, 5 Drawing Figures

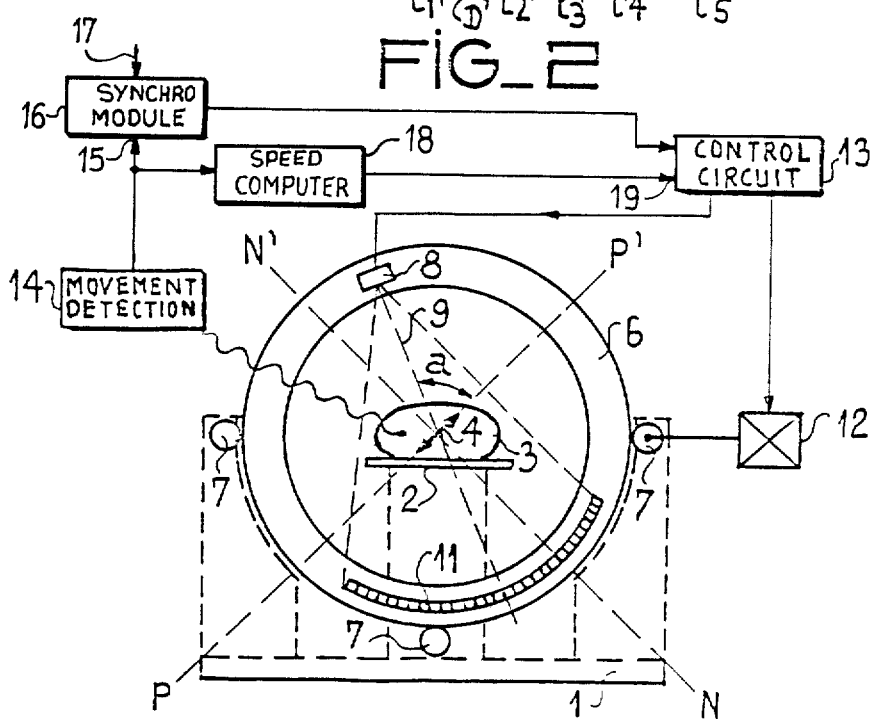

TOMODENSITOMETRY PROCESS AND TOMODENSITOMETER SUITABLE FOR THIS PROCESS

This application is a continuation-in-part of U.S. Ser. No. 144,905, now abandoned, filed Apr. 29, 1980.

BACKGROUND OF THE INVENTION

The invention relates to a tomodensitometry process and to a tomodensitometer suitable for this process. It more specifically relates to a radiodensitometric or tomodensitometric measuring process and to a tomodensitometer for examining bodies performing periodic or cyclic movements, such as cardiac or pericardiac tissues.

Tomodensitometry requires a large number of measurements performed in directions varying according to at least one half-circle. As a result an examination lasts a long time and can even be several minutes. This is not a major disadvantage when it is a question of examining a small organ such as the brain and which is also immobile. However, this no longer applies in connection with the examination of the thorax. Cardiac movements (and breathing) cause blurring which make the examination mediocre or unusable.

In order to obviate this problem attempts have been made to limit the duration of the measurements by using systems having a large number of detectors arranged in fan-like manner. As a result the time can be reduced to several seconds. However, this is still much too long to be included between two cycles when the movements produced by the heart beats are small. It has therefore been proposed to perform the measurements over a random fraction of the cardiac cycle during numerous consecutive cycles. All the measurements are performed on the same fraction, so that a stroboscopic effect is obtained giving a fixed image of the tissue at the chosen moment in the cycle of movement. As far as possible this moment is chosen at the beginning of the period of relative immobility of the heart (diastole) separating two movement periods (systoles).

Although this may well lead to improved results when examining the heart, it is not the case when examining the pericardiac tissues. Thus, the duration of the measurements is greatly increased compared with the case when the measurements were performed continuously, because then they are performed in small series during a large number of fractions of cycles. Throughout the duration of the measurements other movements occur, normally produced by breathing or movements of the patient. Moreover the use of said process leads to the equipment becoming more complicated. Finally this process is limited to the examination of tissues effecting cyclic movements.

BRIEF SUMMARY OF THE INVENTION

The problem of the invention is to provide a process not suffering from these disadvantages. It concerns a process for the tomodensitometry of a body in the vicinity of heart by rotating a radiation source in a plane over at least 180° about said body, the movement of said heart consisting of a sucession of periods of relative immobility and of movement periods, consisting in setting said body in a predetermined position with respect to the rotating path of said source so that a direction of greatest displacement of said heart is approximately determined in said plane, wherein the improvement consists in setting said source in a start position so as to emit in a mean direction substantially perpendicular to said direction of greatest displacement, monitoring the heart beats and synchronizing the starting time of the rotation of said source at a constant velocity so that said source meets said direction of greatest displacement approximately in mid time of a movement period of said heart.

Thus, the problem is solved by a process wherein the movements are at least approximately identified in time and direction and wherein the measurements, in a given mean direction, take place when the projection of the movement in said mean direction is substantially zero.

When there is an inadequate number of linear displacement directions the process remains applicable because the periods of movement are followed by periods of immobility. In this case the measurements are continued during the immobility period following the movement period in directions in which the projection of movements, if they had taken place, would never have been zero.

Since cyclic movements of the heart are divided up in time into periods of movement followed by periods of relative immobility at a substantially fixed frequency the measurements start during an immobility period and are continued during the movement period and the following immobility period. The measurements performed during the movement period take place in a mean direction in which the projection of the movement is substantially zero, i.e. in a direction substantially parallel to that of the movement.

BRIEF DESCRIPTION OF THE DRAWINGS

The invention is described in greater detail hereinafter relative to non-limitative embodiments and the attached drawings, wherein show:

FIGS. 1(a–d) graphs relating to cyclic movements and their effects during measurements represented as a function of time.

FIG. 2 the diagram of a tomodensitometer according to the invention.

DETAILED DESCRIPTION OF THE PREFERRED EMBODIMENTS

The non interrupted line curves of FIG. 1 relate to cardiac movements or to pericardiac tissue movements. The interrupted line curves (A' and D') will be explained further. These movements can be likened to displacements which are substantially linear in a known direction whilst ignoring deformational or rotational movements.

On the ordinate of curve A are shown the amplitude of the movement of the tissue to be examined. It is apparent that a cycle comprises an immobility period from $t_1$ to $t_2$, then a movement period from $t_2$ to $t_4$ with a culminating point at $t_3$. In the case of cardiac movements the immobility periods $t_1 t_2$, $t_4 t_5$ on the one hand and the movement period $t_2 t_4$ on the other in each case last about 0.4 sec.

According to the invention the measurements are started at time $t_1$ and the arrangement is such that at the departure point the mean direction of the rays emitted by the source approximately forms an angle of 90° with the direction of the heart movement as shown. This departure point is empirically determined since the direction of greatest displacement of the heart as evidenced by PP' on FIG. 2, is substantially the same for everybody. Consequently, once a body is lying on a support table 2, direction PP' can be considered as known with a sufficient precision as far as the process is concerned. The rotation time of the measuring assembly has been regulated so that at time $t_5$ it is at its arrival point. For the latter the angle formed by the mean direction of the rays emitted by the source with the direction of the movement is 90°. In a fan like beam, said mean direction of the ray is the direction of the middle of the fan. The angle described by the source between the departure point and the arrival point is approximately 180°.

On curve B is plotted the angle formed by the mean direction of the rays and the direction of heart movement, that is PP'. This curve is a straight line varying from $-90$ to $+90°$ relative to said direction. It should be noted that at time $t_3$ when the mean direction of the rays is parallel to the direction of the movement the latter is at its maximum amplitude (curve A). Curve C shows on the ordinate the sine value of the angles shown on the ordinate of curve B.

The effect of the movement on the measurements is proportional to the product of the amplitude of the movement (curve A) by the sine of the angle formed by the mean direction of the rays and the direction of the movement (curve C). The values of this effect are plotted on curve D. It can be seen that as from $t_1$ to $t_2$ and from $t_4$ to $t_5$ the movement is zero, its effect is zero. From $t_2$ to $t_3$ and from $t_3$ to $t_4$ the effect is not zero, but it is low due to the low sine value.

By using the process of the invention and performing the measurements between the start of an immobility period and the end of a following immobility period and proceeding in such a way that the mean direction of the rays is parallel to the direction of movement at the time when the movement is at its maximum amplitude the movement has a very limited effect on the measurements. Moreover, the total duration of the movements is short and in fact approximately 1.5 sec. because they are performed without interruption from start to finish, even during the movement period. This short duration makes it possible to eliminate movements produced by causes other than the beating of the heart, e.g. breathing or any other movement of the body being examined.

Curves A' illustrates a periodic movement without immobility periods and corresponds to an essentially linear displacement in an identified direction. According to the invention, the measurements are started at time $t_1$, the mean direction of the rays emitted by the source forming an angle of 90° with the direction of said movement. The point $t_1$ does not correspond exactly to the start of an immobility period but rather to the start of very small movement period $t_1-t_2$. Thus, curve D' which is the product of the amplitude of the movement (curve A') by the sine of the angle formed by the mean direction of the beam and the direction of heart movement (curve C) is always low as evidenced by curve D' on FIG. 1d.

FIG. 2 is an apparatus suitable for this process.

A base 1 supports an examination table 2 on which is placed the body 3 to be examined. The body area to be examined performs elementary cyclic movements along a segment 4, whose orientation, PP' is substantially in the examination plane and is approximately known as explained above once the body is on the table 2. A measuring system represented by a ring 6 rolling on rollers 7 fixed to base 1 incorporates a source 8 which emits a fan-like beam of X-rays, whose mean direction indicated by dotted line 9 forms an angle a with line PP' in the direction of a system of measurement detectors. The ring rotates and causes the source to rotate in a plane transverse to the body. The orientation of the measuring system about an axis subtantially parallel to the plane of examination table 2 is controlled by a motor 12, itself controlled by a control circuit 13. A cyclic movement detection apparatus 14, which can be an electrocardiograph, is connected to the body 3 to be examined. It transmits signals to a validation input means 15 of a synchronization module 16. At a control input means 17, module 16 receives the signals concerning the start of the measurements coming from an operator. As a function of the signals received from detection apparatus 14 and the operator 17 module 16 transmits to control circuit 13 the signals necessary for initiating and performing the measurements. More precisely, said synchronization module 16 comprises delay means to delay control signal from the operator to be transmitted to control circuit 13 up to a next period of relative immobility. Then circuit 13 controls both the emission of source 8 and the starting of motor 12 at a constant velocity.

According to a preferred embodiment, the system also includes a speed computer 18 connected between the output of movement detection apparatus 14 and a data input 19 of said control unit. This speed computer is designed to compute the rotation speed of motor 12 so that the ring 6 driven thereby performs a 180° rotation at a constant velocity during time interval $t_1-t_5$ corresponding to the sum of two periods of relative immobility ($t_1-t_2$, $t_4-t_5$) and one movement period ($t_2-t_3$).

Control circuit 13 comprises conventional variation speed means to control motor 12 as a function of duration $t_1-t_5$ of the examined body 3. However, considering that cardiac rhythm is almost the same for everybody, the speed computer 18 may be omitted and the speed of motor 12 may be a predetermined constant value corresponding to a mean heart cyclic rate.

The apparatus functions as follows. Synchronization module 16 receives from detection apparatus 14 signals identical to the shape of curve A' (FIG.1) giving the start and finish of each period of movement and relative immobility. It processes and transmits to the control circuit 13 a signal such that the measuring system performs a rotation of about 180° during the time $t_5-t_1$.

Before starting the measurements the operator displays a position for the start of the measurements at N corresponding to a position where the mean direction of the rays 9 approximately forms an angle of 90° with segment 4.

When at 17 the operator transmits the measurement starting signal, module 16 does not transmit it directly to circuit 13. Instead it delays the signal and only transmits it when detection apparatus 14 has indicated the start $t_1$ of a relative immobility period. Meanwhile, computer 18 has transmitted data information concerning the speed to which motor 12 must be driven so that, during rotation of ring 6 at a constant velocity, said source meets direction PP' of greatest heart displacements approximately in mid time ($t_3$) of a movement period of heart. Circuit 13 then transmits the transmission signal to the source and operates the motor, so that the measuring system reaches its departure position at N at time $t_1$ and at its arrival position at N' at time $t_5$, which is the end of the following relative immobility period.

The invention is obviously not limited to the embodiment described hereinbefore. Thus, for performing the measurements it is not necessary to use all the immobility periods preceding and following the movement. There is also no need to choose as the starting position for the measurements that in which the mean direction of the rays is perpendicular to the direction of the movement. The measurements can be started and finished at random times in the cycle, provided that when the movement takes place the mean direction of the rays substantially coincides with that of the movement. Moreover the process of the invention can also be used for the examination of tissues other than cardiac or pericardiac tissues. It can also be used for non-medical examinations, for example, the examination of bodies whose movements can be broken down into a series of linear paths.

The invention can also be applied to tomodensitometers in which the measuring assembly incorporates a plurality of X-ray sources distributed over a circle or a portion of a circle about the examined object so as to limit or eliminate the rotational movement of the system formed by the source and the detectors. The elimination of the rotational movement is particularly advantageous in the case where the object or part of it performs successive substantially linear movements in a large number of different directions. The synchronization module and the control circuit are then realized in such a way that when a movement is detected the tube, which is essentially in the extension of the direction of the movement emits a beam of X-rays towards the object.

To eliminate the rotational movement of the source-detectors system and to obviate the use of a plurality of X-rays tubes it is also possible to use a single tube in which the circular or semi-circular anode surrounding the object is scanned by one or more beams of electrons emitted by one or more cathodes.

What is claimed is:

1. A process for the tomodensitometry of a body, in the vicinity of a heart, by rotating a radiation source in a plane over at least 180° about said body, the movement of said heart consisting of a succession of periods of relative immobility and of movement periods, consisting in setting said body in a predetermined position with respect to the rotating path of said source so that a direction of greatest displacement of said heart is approximately determined in said plane, wherein the improvement consists in setting said source in a start position so as to emit in a mean direction substantially perpendicular to said direction of greatest displacement, monitoring the heart beats and synchronizing the starting time of the rotation of said source at a constant velocity so that said source meets said direction of greatest displacement approximately in mid time of a movement period of said heart.

2. A process according to claim 1 wherein said constant velocity is computed on the basis of the duration of two aforesaid periods of relative immobility and one aforesaid movement period.

3. A process according to claim 1 wherein said constant velocity is a predetermined value.

4. A process according to claim 1 wherein said starting time is substantially the beginning of an aforesaid period of relative immobility.

5. A tomodensitometer system for performing a tomodensitometric process on a body, in the vicinity of a beating heart, wherein said beating heart has a succession of periods of relative immobility and of movement, said system comprising:

a rotatable radiation source;

means for supporting said source;

table means supporting said body wherein said radiation source is rotatable over at least 180° about said body in a plane intersecting a portion of said beating heart which portion includes the part of said heart exhibiting the greatest displacement during a heart beat;

heart movement detector means coupled to said body to provide a validation output;

synchronization means having a first input for receiving an operator signal and second input for receiving said validation output wherein said synchronization means outputs a synchronization signal; and control circuit means having a first input for receiving said synchronization signal and a data input wherein said control circuit means outputs a signal to operate a drive motor means to drive said source support means at a constant velocity and wherein said control circuit, said synchronization means and said data input provide for a synchronization of the starting time of the rotation of said source and a constant velocity so that said source meets said direction of greatest displacement of said heart approximately at a mid point in each of said movement periods of said heart.

6. A tomodensitometer according to claim 5 further comprising a speed computer connected between the output of said movement detector means and said data input of said control circuit means.

7. A tomodensitometer according to claim 5 wherein said control circuit means controls said drive motor means at a predetermined constant velocity corresponding to a mean heart cyclic rate.

* * * * *